United States Patent [19]

MacDougall

[11] Patent Number: 4,822,347
[45] Date of Patent: Apr. 18, 1989

[54] FEMALE INCONTINENCE DEVICE

[75] Inventor: Morag M. MacDougall, London, England

[73] Assignee: E. R. Squibb and Sons, Inc., Princeton, N.J.

[21] Appl. No.: 336,244

[22] Filed: Dec. 31, 1981

[30] Foreign Application Priority Data

Jan. 14, 1981 [GB] United Kingdom ............... 8101033

[51] Int. Cl.⁴ .............................................. A61F 5/44
[52] U.S. Cl. ................................. 604/329; 604/336; 4/144.3
[58] Field of Search .................. 4/144.1, 144.2, 144.3, 4/144.4; 128/761, 766, 767, 768, 769; 604/317, 326, 327, 329, 332, 338, 339, 355, 343–345

[56] References Cited

U.S. PATENT DOCUMENTS

| | | | |
|---|---|---|---|
| 3,194,238 | 7/1965 | Breece | 128/295 |
| 3,200,415 | 8/1965 | Breece, Jr. | 4/144.2 |
| 3,339,546 | 9/1967 | Chen et al. | 128/156 |
| 3,340,876 | 9/1967 | Hill | 128/767 |
| 3,349,768 | 10/1967 | Keane | 128/276 |
| 3,374,790 | 3/1968 | Mayhorne | 128/295 |
| 3,421,506 | 1/1969 | Webb et al. | 4/144.3 |
| 3,421,507 | 1/1969 | Graham | 604/349 |
| 3,512,185 | 5/1970 | Ellis | 4/110 |
| 3,523,537 | 8/1970 | Hill | 128/767 |
| 3,556,102 | 1/1971 | Davis | 604/329 |
| 3,577,989 | 5/1971 | Anderson | 128/283 |
| 3,651,810 | 3/1972 | Ormerod | 604/329 |
| 3,661,155 | 5/1972 | Lindan | 128/295 |
| 3,683,914 | 8/1972 | Crowley | 128/285 |
| 3,776,235 | 12/1973 | Ratcliffe et al. | 128/295 |
| 4,198,979 | 4/1980 | Cooney et al. | 604/329 |
| 4,233,978 | 11/1980 | Hickey | 128/295 |
| 4,270,539 | 6/1981 | Michaud | 128/295 |

FOREIGN PATENT DOCUMENTS

| | | |
|---|---|---|
| 2506477 | 11/1978 | Australia . |
| 2721330 | 11/1977 | Fed. Rep. of Germany . |
| 994274 | 2/1965 | United Kingdom . |
| 1144483 | 11/1969 | United Kingdom . |
| 1193261 | 9/1970 | United Kingdom . |
| 1422638 | 3/1976 | United Kingdom . |
| 1476144 | 3/1977 | United Kingdom . |
| 2015347 | 8/1979 | United Kingdom . |

*Primary Examiner*—John D. Yasko
*Assistant Examiner*—J. L. Kruter
*Attorney, Agent, or Firm*—Lawrence S. Levinson; Robert E. Lee, Jr.

[57] ABSTRACT

An incontinence device for females is intended for long term wear. It includes a tubular sheath integral with a funnel and a urine-conducting pipe. The sheath is secured to a pad of adhesive material having a central hole leading into the interior of the sheath. The pad is dimensioned so that it can be stuck to the skin of the wearer in the region immediately surrounding the urethral orifice (meatus).

3 Claims, 1 Drawing Sheet

FEMALE INCONTINENCE DEVICE

BACKGROUND OF THE INVENTION

There have been a very large number of prior proposals for devices intended to be worn by females who suffer from urinary incontinence. Some of these prior proposed female incontinence devices have involved the provision of a support structure which is inserted in the vagina to hold the device in place. Examples of this kind of device are shown in U.S. Pat. Nos. 3,776,235 to Ratcliffe et al., 3,661,155 to Linden, and 3,683,914 to Crowley. In some cases it is intended to obtain close engagement with, and possibly even sealing at, the immediate surround of the urethral orifice. Devices having a substantial support structure within the vagina are often uncomfortable to wear, and the intended sealing at the urethral orifice is often not effective. Anatomical variations from person to person mean that any effective device must be tailored to the individual user.

Other devices proposed in the prior art are of the kind which are brought into engagement with the external urine-genital region, there being a sealing rim or pad intended to prevent escape of urine between the device and its wearer. Examples of this kind of device are shown in U.S. Pat. Nos. 3,349,768 to Keane and 3,512,185 to Ellis and U.K. Patent Specification Nos. 1,193,261 to Dent, 1,144,483 to Vincent, and 1,422,638 to Lowthian. Person-to-person variations also give rise to difficulty here, and it has proved difficult to obtain effective sealing in practice (despite the claims made in the prior art documents) especially when the device is being worn by an active person.

SUMMARY OF THE INVENTION

According to this invention, there is provided an incontinence device for females including a tubular sheath integral with a funnel and a urineconducting pipe, which sheath is secured to a pad of adhesive material as herein defined and having a central hole leading into the interior of the sheath. The pad is dimensioned so that it can be stuck to the skin of the wearer in the region immediately surrounding the urethral orifice (meatus).

DETAILED DESCRIPTION OF THE INVENTION

Figure 1:
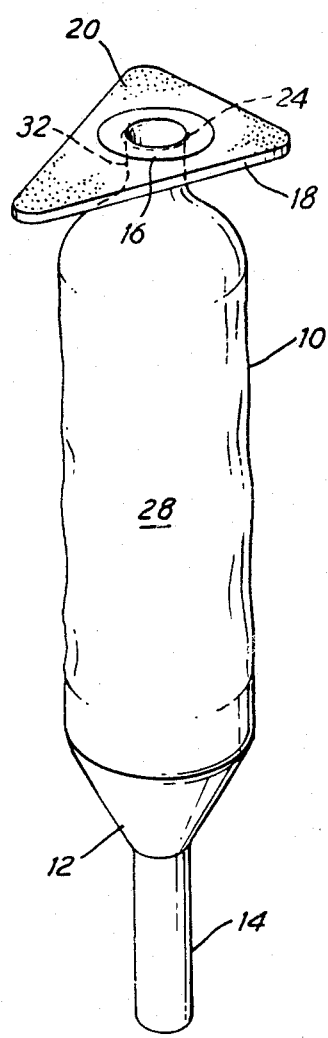
FIG. 1 is a perspective view of one example of female incontinence device according to this invention.

The illustrated female incontinence device includes a tubular sheath 10 integral with a funnel 12 and a urine-conducting pipe 14. The tubular sheath resembles a male condom except at its lower end and may have its upper end strengthened by a beading 16. The presence of the beading is of advantage in producing a good seal with the adjacent skin surface. The upper end is secured in any convenient manner, for example by a separate adhesive, to a pad 18 of adhesive material as herein defined. The upper end of the sheath may alternatively be adhesively secured to the lower (non-skin-engaging) surface 22 of the pad 18, if desired for ease of manufacture, but the illustrated construction is presently believed to be stronger. The sheath preferably takes the form illustrated, having an entry portion 32 of cross-sectional area approximately equal to the area of a circle of 0.8 to 1.0 cms. diameter, and this portion opens out into a substantially cylindrical chamber 28 which can be regarded as a "surge chamber" capable of accepting a sudden large flow of urine. Such a chamber may be about 11-16 cms. long and have an unstretched diameter of 2-3 cms. It preferably has a wall thickness of only two or three thousandths of an inch (e.g., 0.025-0.1 mm.) and, being made of latex rubber is highly stretchable. This enhances the capability to accomodate surges of urine, and reduces the chance of surges of urine tending to detach the adhesive surface of the pad 18 from the wearer. At the same time, the device is unobtrusive and not uncomfortable to wear.

The pad 18 has a shape and configuration chosen to be appropriate to the average female genital anatomy, and has a first adhesive surface 20 and a second surface 22 which is non-adhesive. In one particular embodiment of the invention, the pad 18 is generally triangular in shape with rounded corners, the triangle being an isosceles triangle with sides of lengths in the ranges 2-3.5 cms., 2-3.5 cms., and 1.5 to 2.75 cms. The pad 18 is preferably fairly thin, e.g., having a thickness of about 15 to 30 thousandths of an inch, say 0.3 to 0.8 mm.

The pad 18 has an adhesive surface 20 which is capable when applied to moist body skin surfaces, of adhesively adhering thereto for a prolonged period of time, for example, well over 12 hours, and which at the same time, for the majority of human beings, does not generate any allergic reaction or irritation when so adhered.

Preferably, the adhesive surface 20 is a homogeneous blend of one or more water soluble or water swellable hydrocolloids dispersed in a water insoluble, viscous elastic binder and the non-adhesive surface 22 is a thin film of polymeric material Suitably adhesive pads are described by Chen in U.S. Pat. No. 3,339,546 and by Chen et al. U.S. Pat. No. 4,192,785. One suitable adhesive material is commercially available under the trademark Stomahesive and consists of a blend of sodium carboxymethylcellulose, gelatin, and pectin dispersed in polyisobutylene with a thin polyethylene film laminated to one surface of the adhesive.

Figure 2:
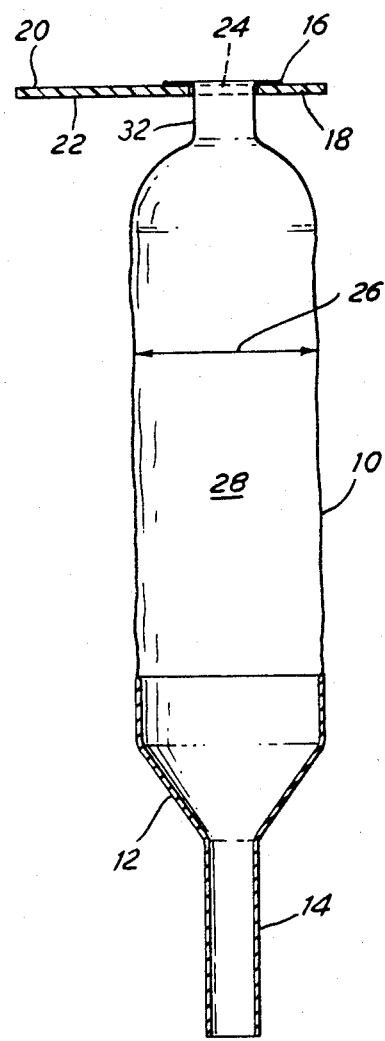
FIG. 2 is a medial vertical cross-section of the device shown in FIG. 1.

One possible method of assembly is illustrated in FIGS. 1 and 2. The open end of the sheath is passed through a hole 24 in the pad 18 and is turned over and secured to the pad 18 as mentioned above. Typical dimensions for the pad would be, for a pad of generally elliptical shape, a thickness of from ½ to 2 mm, a length along its major axis of from 3 to 6 cm., and a width along the minor axis of 1½ to 4 cms. In the undeformed condition of the tubular sheath its internal diameter at the point indicated 26 in FIG. 2 would be about 2 or 3 cm.

The tubular sheath is prepared of latex rubber by a conventional dipping operation, and the funnel 12 which is integral therewith at its lower end is formed by building up extra layers so making a greater wall thickness. The outlet part 14 is likewise built up by multiple dipping operations.

In use, the adhesive surface 20 is applied to the region surrounding the urethral meatus, and a conventional conduit or pipe is attached to the conduit 14 and is arranged to lead to a leg bag or to a urine collection vessel, as may be appropriate.

An advantage of the particular construction disclosed is that the substantial volume available in the region indicated 28 accommodates the initial surge of urine which may occur, and hence there is not a build-up of pressure of urine tending to pull the adhesive surface 20 away from its adjacent skin. The tubular sheath 10 is of a thin, flexible baggy nature and it is a particular point of the present invention that the wall thickness of the sheath should be small, for example under 0.1 mm. This makes the device comfortable and unobtrusive to wear, in contrast to many of the rigid devices according to the prior art discussed above. The fact that the tubular sheath is stretchable under applied pressure also assists in accommodating any sudden surge of urine. The feature of adhesively securing the pad 18 around the orifice of the urethra enables the device to be made small in size and easily applied and removed. No medical assistance is required for insertion or removal. In prior art devices, numerous complicated structures and arrangements have been suggested for holding female incontinence devices in their working positions. Such complex and intrusive arrangements are avoided by the invention as particularly disclosed and illustrated herein.

What is claimed is:

1. An incontinence device for females consisting of an adhesive pad having an upper adhesive layer that in use contacts the body and a lower non-adhesive side, said upper adhesive layer of said pad comprising a homogeneous blend of one or more water soluble or swellable hydrocolloids in a viscous elastic binder and said lower non-adhesive side of said pad is a film of polymeric material, said pad is dimensioned so that it can be stuck to the skin of the wearer in the region immediately surrounding the urethral orifice, said pad having a centrally located aperture through said adhesive layer and said non-adhesive side, and a tubular sheath having an upper end that is strengthened by beading and a lower end that is integral with a funnel that empties into a urine-conducting pipe, said tubular sheath including a cylindrical chamber intermediate to said upper and lower ends, wherein the upper end of said sheath has a narrower diameter then said cylindrical chamber and passes through the aperture in said adhesive pad and said beading is adhesively secured to the adhesive layer of said pad.

2. A device according to claim 1 wherein said sheath is latex rubber having a wall thickness from about 0.025 to about 0.1 mm., said narrow diameter upper end is from about 0.8 to 1.0 cm., and the remaining cylindrical sheath portion is from about 11 to about 16 cm. long and has an unstretched diameter of from about 2 to about 3 cm.

3. A device according to claim 1 wherein said adhesive pad is generally triangular in shape with rounded corners, said triangle being an isosceles triangle with sides of lengths in the ranges 2 to 3.5 cms., 2 to 3.5 cms., and 1.5 to 2.75 cms. and said pad having a thickness of about 0.3 to 0.8 mm.

* * * * *